United States Patent
Goldstein et al.

[11] Patent Number: 5,810,746
[45] Date of Patent: Sep. 22, 1998

[54] GUIDING INTRODUCER FOR ENDOMYOCARDIAL BIOPSY PROCEDURES

[75] Inventors: James A. Goldstein, Royal Oaks, Mich.; John J. Fleischhacker, Minnetonka, Minn.

[73] Assignee: Daig Corporation, Minnetonka, Minn.

[21] Appl. No.: 749,339

[22] Filed: Nov. 21, 1996

[51] Int. Cl.$^6$ .................................................. A61B 5/00
[52] U.S. Cl. ............................................................ 600/585
[58] Field of Search ................................... 128/657, 658, 128/772; 604/95, 96, 280, 281, 282, 283

[56] References Cited

U.S. PATENT DOCUMENTS

| | | | |
|---|---|---|---|
| 3,964,468 | 6/1976 | Schulz | 128/2 B |
| 4,945,920 | 8/1990 | Clossick | 128/751 |
| 5,273,051 | 12/1993 | Wilk | 128/751 |
| 5,287,857 | 2/1994 | Mann | 128/753 |
| 5,306,263 | 4/1994 | Voda | 604/281 |
| 5,318,528 | 6/1994 | Heaven et al. | 604/95 |
| 5,427,119 | 6/1995 | Swartz et al. | 128/772 |
| 5,497,774 | 3/1996 | Swartz et al. | 128/658 |
| 5,639,276 | 6/1997 | Weinstock et al. | 606/129 |
| 5,656,028 | 8/1997 | Swartz et al. | 604/53 |

OTHER PUBLICATIONS

Baraldi–Junkins, C. et al. "Complications of Endomyocardial Biopsy in Heart Transplant Patients" The Journal of Heart and Lung Transplantation, pp. 63–67 (1993).

Huddleston, C. et al. "Biopsy–Induced Tricuspid Regurgitation After Cardiac Transplantation" The Society of Thoriacic Surgeons, pp. 832–837 (1994).

Product Literature: pp. 51A, 57 and 57A of the 1995 Daig Product Catalog.

*Primary Examiner*—Max Hindenburg
*Assistant Examiner*—Charles Marmor, II
*Attorney, Agent, or Firm*—Scott R. Cox

[57] ABSTRACT

A guiding introducer for use with an endomyocardial biopsy forceps is disclosed. The guiding introducer is precurved to assist in the support and placement of biopsy forceps or a bioptome in the correct location within the heart for biopsy procedures, preferably the right ventricle.

23 Claims, 3 Drawing Sheets

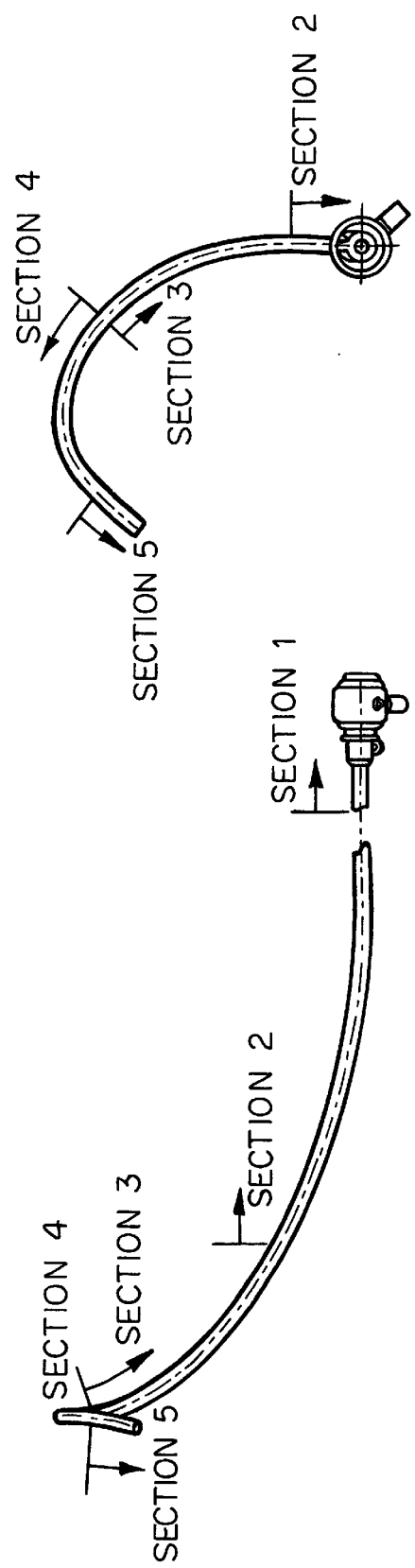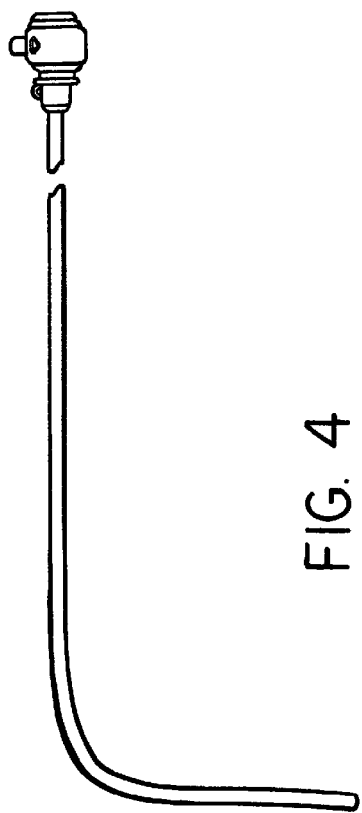
FIG. 2
FIG. 3
FIG. 4

GUIDING INTRODUCER FOR ENDOMYOCARDIAL BIOPSY PROCEDURES

BACKGROUND OF INVENTION

1. Field of Invention

This invention discloses a medical device for use in a human heart. More specifically, this invention relates to a precurved, guiding introducer for use with biopsy forceps to perform endomyocardial biopsy procedures in the human heart.

2. Prior Art

Biopsy procedures are commonly performed to obtain tissue samples from various locations within the human body. In particular, heart biopsies, such as endomyocardial biopsies, are now the accepted procedure after a heart transplant to test for tissue rejection. In an article, Baraldi-Junkins, C., et al. "Complications of Endomyocardial Biopsy in Heart Transplant Patients," *The Journal of Heart and Lung Transplantation*, pages 63–67(1993), the number of heart transplant recipients reported was over 10,000, performed in 173 centers worldwide. These endomyocardial biopsy procedures have proven to be a simple, reliable and quick method for biopsing the tissue of the heart. Complications of the procedure are relatively few and relate generally to irritation at the site of insertion in the body of the biopsy equipment.

One biopsy forceps commonly used for performing endomyocardial biopsies is a Schulz-Caves bioptome. See U.S. Pat. No. 3,964,468. Other biopsy forceps or bioptomes are disclosed, for example, in U.S. Pat. Nos. 5,318,528 and 4,945,920. Alternative biopsy devices are disclosed in U.S. Pat. Nos. 5,287,857 and 5,273,051.

To perform an endomyocardial biopsy procedure, a cannula is inserted into the jugular vein through an incision at the base of the neck of the patient. (The insertion site can also be the subclavian or femoral vein.) A flexible guidewire is then inserted through the cannula into the vein and the cannula is then removed. A sheath or introducer is then inserted over the guidewire through the vein into the chamber of the heart used for the biopsy procedures, normally the right ventricle. A catheter containing the biopsy forceps or bioptome is then introduced into the vein through the introducer or sheath.

The introducer or sheath that has commonly been used for endomyocardial biopsy procedures through the jugular vein is a 45 centimeter introducer such as is sold by Daig Corporation under the name Fast Cath™ Hemostasis Introducer. A curved introducer or sheath that has also been used with biopsy forceps for endomyocardial biopsy procedures is a "hockey stick" shaped sheath produced by Cordis Corporation. This sheath is disclosed, for example, in FIG. 3 of Huddleston C. B., et al. "Biopsy-Induced Tricuspid Regurgitation After Cardiac Transplantation," *The Society of Thoracic Surgeons*, Vol. 57, pages 832–37 (1994). This sheath is a standard 45 cm. introducer, the distal portion which has been bent at an angle of about 60° from the straight, proximal portion of the sheath. While this sheath has been useful in performing endomyocardial biopsy procedures, improvements to its shape are necessary. In particular, this "hockey-stick" shaped sheath does not place the biopsy forceps at the precise location within the heart for the biopsy procedure. In addition, when using this "hockey-stick" shaped sheath, as the biopsy forceps are extended from the distal end of the sheath, it tends to "float" about in the right ventricle. As the forceps extend past the tip of the sheath unsupported, the forceps tend to move side-to-side or up and down within the heart chamber depending on the flow of the blood within that heart chamber.

Almost all endomyocardial biopsies are performed in the right ventricle, although some can be performed in the left ventricle. The desired location within the right ventricle from which to obtain the tissue to be biopsied is the septum of the heart. Because of the anatomy of many transplanted hearts, it is frequently difficult to place the biopsy forceps in the precise location in the heart to obtain this sample. In addition, particular areas of the transplanted heart are especially susceptible to injury as a result of the transplant. Typically, the valve structure, such as the tricuspid valve, must be carefully negotiated during the endomyocardial biopsy procedure to avoid damage to the valve. New introducers are thus necessary which address these problems.

Accordingly, it is an object of this invention to disclose a shaped introducer or sheath for introducing an endomyocardial biopsy catheter into a human heart.

It is another object of this invention to disclose a shaped endomyocardial biopsy sheath or introducer which will place the biopsy forceps directly adjacent to the septum to perform the biopsy procedure.

It is a still further object of this invention to disclose a shaped endomyocardial biopsy sheath or introducer for use with biopsy forceps which will reduce the likelihood of trauma to the tricuspid valve during the endomyocardial biopsy procedure.

It is a still further object of this invention to reduce the time necessary for performing endomyocardial biopsy procedures by use of a shaped endomyocardial biopsy sheath or introducer during the procedure.

It is a still further object of this invention to disclose a shaped endomyocardial biopsy sheath or introducer which provides a stable platform supported against the cardiac anatomy to permit biopsy forceps to be repeatedly advanced and withdrawn from the introducer during the procedure without the need for repositioning the introducer.

These and other objects of the invention will be apparent from the drawings and specifications disclosed in the instant invention.

SUMMARY OF INVENTION

The instant invention discloses a precurved, guiding introducer for use with an endomyocardial biopsy catheter for obtaining biopsy samples from the wall of the human heart. This precurved, guiding introducer has a unique three dimensional shape divided into a first, second, third, fourth and fifth sections, each with a separate and distinct shape.

BRIEF DESCRIPTION OF THE DRAWINGS

FIG. 2 is an end view of the guiding introducer with a hemostasis valve attached to its proximal end, wherein the hemostasis valve housing has been rotated about 50° clockwise below a horizontal plane passing through the proximal end of the introducer.

FIG. 3 is a side view of the guiding introducer of FIG. 2, wherein the guiding introducer has been rotated 90° clockwise about a vertical axis running through the proximal end of the introducer, when the guiding introducer is viewed from the perspective of its proximal end.

FIG. 4 is a side view of the guiding introducer of FIG. 3, wherein the guiding introducer has been rotated 90° clockwise about a horizontal axis running through the proximal end of the guiding introducer, when the guiding introducer is viewed from the perspective of its proximal end.

DESCRIPTION OF THE INVENTION

Heart transplants are becoming more common. In 1992 there were over 170 heart transplant centers worldwide with over 10,000 transplant patients. After the initial trauma, the most significant medical concern for patients who have had heart transplants is the risk of tissue rejection. To monitor the possibility of rejection, biopsy samples of the heart tissue are conventionally taken immediately following the transplant. These biopsy procedures commonly continue once a week for the first eight weeks and then once every two weeks for an extended period of time. Even in the absence of any evidence of tissue rejection, as many as 15 to 20 biopsy procedures are normally performed during the first 12 months after a transplant.

Conventionally, five separate tissue samples are gathered during each biopsy procedure. Each time a tissue sample is obtained, it must be withdrawn from the heart and placed in a container. Using conventional biopsy devices, the entire biopsy procedure normally takes at least 30 minutes. Because the patient is awake during the entire biopsy procedure, having received only local anesthesia, it is important to reduce the time of the procedure as much as possible. The device disclosed below assists in the performance of the biopsy procedure and reduces the time necessary for this procedure to 10 minutes or less.

A typical human heart includes a right ventricle, a right atrium, a left ventricle and a left atrium. The right atrium is in fluid communication with the superior vena cava and the inferior vena cava. The atrio ventricular septum separates the atria from the ventricles. The tricuspid valve contained within the atrial ventricular septum communicates the right atrium with the right ventricle.

Figure 1:
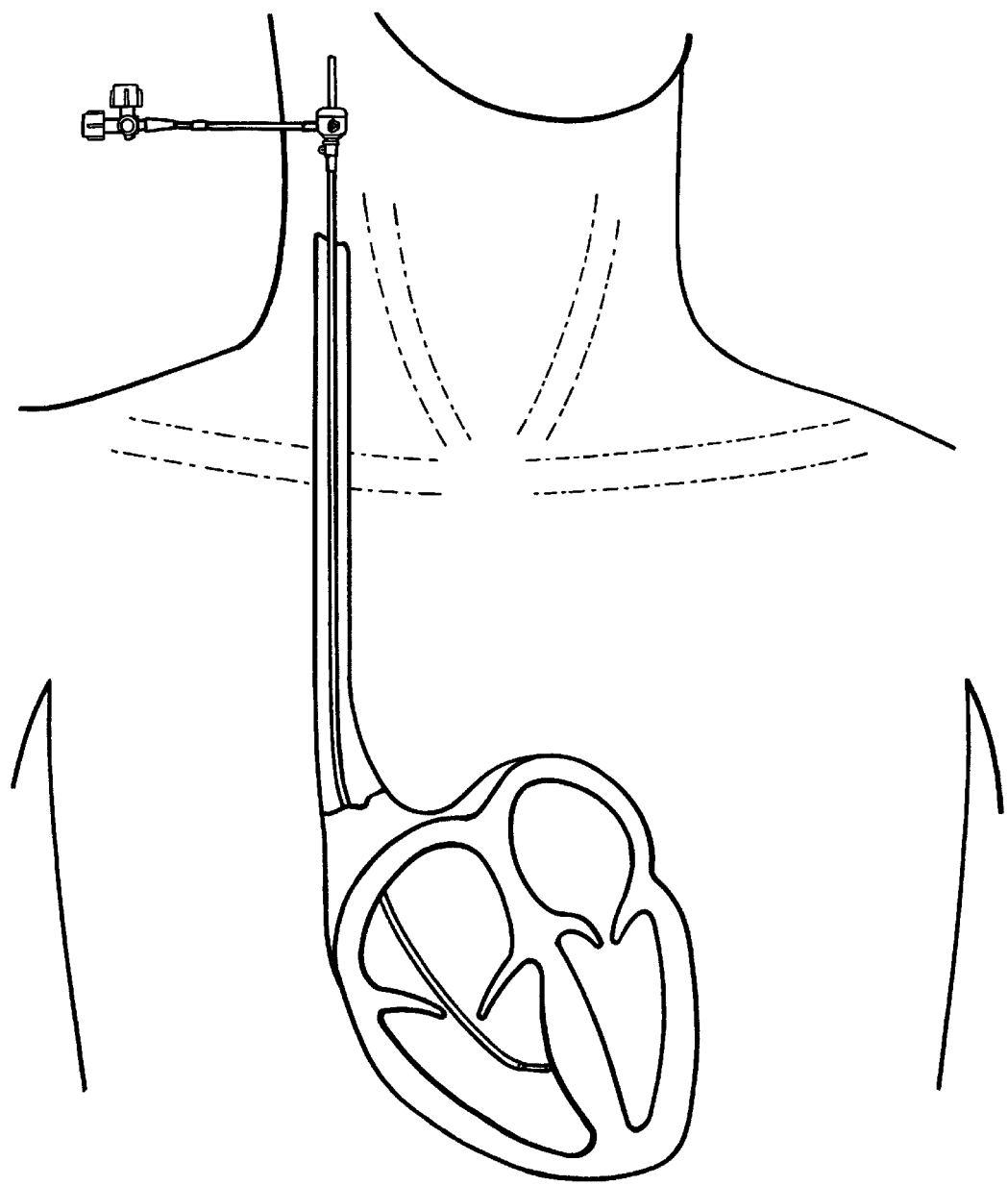
FIG. 1 is a cutaway view of the upper torso of a human body showing the precurved guiding introducer for use with endomyocardial biopsy forceps in place in the human body.

Endomyocardial biopsy procedures are preferably performed in the right ventricle of the transplanted heart, although they may be performed in the left ventricle. The biopsy procedures are preferably performed using a superior approach through either the internal jugular or subclavian vein. Alternatively, an inferior approach can be used through the femoral vein. During the superior approach, an introducer for the biopsy forceps is inserted into the vein and directed through the superior vena cava into the right atrium across the tricuspid valve into the right ventricle. The biopsy forceps are then passed through the introducer to emerge in the right ventricle to remove the samples of heart tissue from the septum. The guiding introducer discussed below is specifically designed for this superior approach to the right ventricle. See FIG. 1.

Existing introducers used with biopsy forceps are not sufficiently stable for use in the right ventricle and tend to float about the chamber as the blood is being pumped. Proper placement of the biopsy forceps is important and is achieved by use of the precurved guiding introducer disclosed herein.

The shape of the guiding introducer for use with biopsy forceps or bioptomes will now be discussed in detail. Referring to FIGS. 2 through 8, the precurved, guiding introducer of the present invention for use in the introduction of a bioptome or biopsy forceps into the human heart is comprised of a first, second, third, fourth and fifth sections. (Each section is preferably formed as an integral portion of the entire guiding introducer without discrete divisions. However, the division of the guiding introducer into different sections better illustrates the overall shape of the guiding introducer.) The guiding introducer is shown in a number of views. See Exhibits 2–8. In each of the views, the guiding introducer will be secured to a conventional hemostasis valve with side port. In each such arrangement, the shape of the guiding introducer and each of its sections will be described, making reference to its position in relation to the hemostasis valve secured to the proximal end of the guiding introducer.

In the first view (FIG. 2), the guiding introducer is viewed from its proximal end. The hemostasis valve with side port is attached to the proximal end of the guiding introducer. The side port is directed at an angle rotated about 50° clockwise away from a horizontal plane passing through the proximal end of the guiding introducer. In the second view (FIG. 3) the guiding introducer is rotated clockwise about 90° about a vertical axis passing through the proximal end of the guiding introducer of FIG. 2, when viewed from the perspective of the proximal end of the guiding introducer. In the third view (FIG. 4) the guiding introducer is rotated clockwise 90° about a horizontal axis passing through the proximal end of the guiding introducer shown in FIG. 3 when viewed from the perspective of the proximal end. Each section of the guiding introducer is labeled in these figures for ease of reference.

Figure 5:
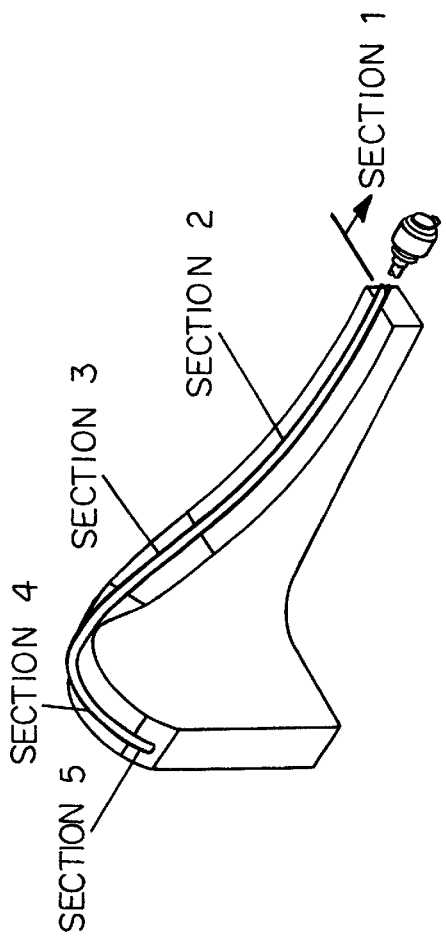
FIG. 5 is a perspective view of the guiding introducer placed against the background of a block structure.
Figure 6:
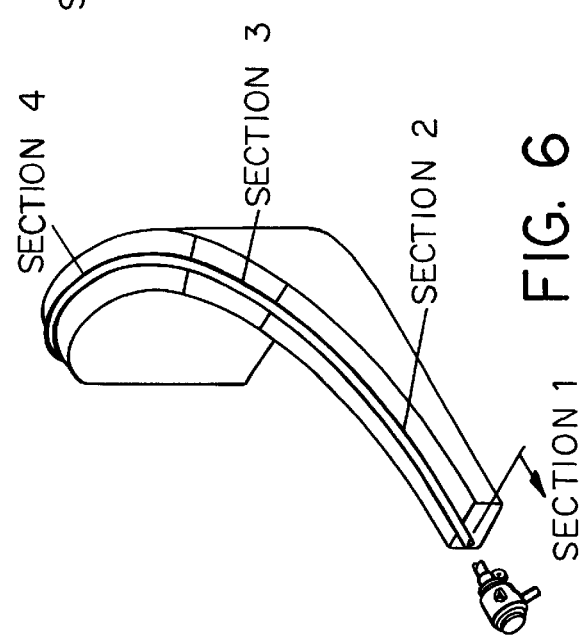
FIG. 6 is a second perspective view of the guiding introducer of FIG. 5 rotated 90° about a vertical axis from its position in FIG. 5.
Figure 7:
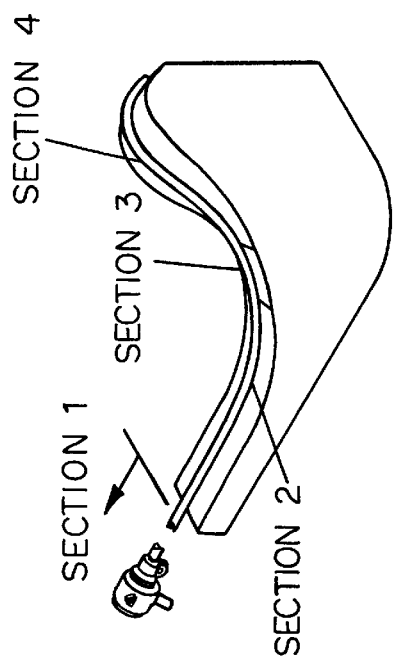
FIG. 7 is a third perspective view of the guiding introducer of FIG. 5 rotated 90° about a vertical axis from its position in FIG. 6.
Figure 8:
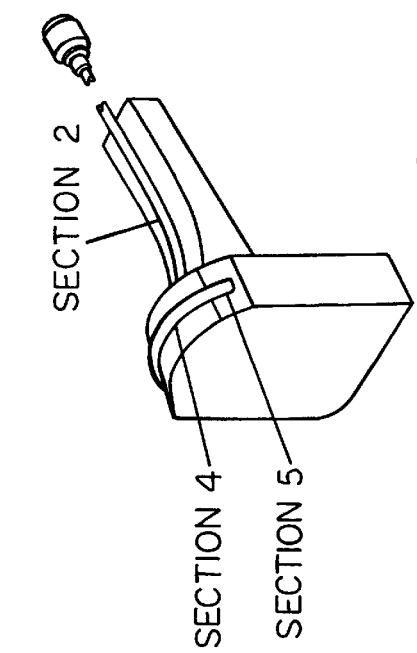
FIG. 8 is a fourth perspective view of the guiding introducer of FIG. 5 rotated 90° about a vertical axis from its position in FIG. 7.

Four additional, perspective views of the guiding introducer are shown in FIGS. 5, 6, 7 and 8. In each of these views, the guiding introducer is laid against a three dimensional block background which better discloses the curvature of the individual sections of the guiding introducer. The sections of the block are labeled for easier reference to the sections of the guiding introducer. In each view, the guiding introducer is placed on the block background approximately in the position shown in FIG. 2. FIG. 6 is rotated 90° clockwise about a vertical axis, passing through the distal end of the guiding introducer from its position in FIG. 5 when viewed from the perspective of the proximal end. FIG. 7 is rotated an additional 90° about the vertical axis from the position of FIG. 6. FIG. 8 is rotated an additional 90° from its position in FIG. 7.

The first section of the guiding introducer is a hollow, generally straight section of sufficient length for introduction into the patient and for manipulation from the point of insertion to the specific desired location within the heart.

Merged with the distal end of the first section of the guiding introducer is the second section which comprises a curved portion as shown in the perspective views in FIGS. 5, 6, 7 and 8 against that portion of the block labeled "section 2." This curve is also shown as "section 2" on FIG. 3. This second section is a curve with a radius from about 2 to about 8 inches, preferably from about 4 to about 6 inches. The extent of the arc of the curve of this curved section is from about 20° to about 70° and preferably from about 40° to about 50°.

Following this second section is the third section which forms a compound curved section, curving both upward and to the left as shown against that portion of the block background labeled "section 3" in FIGS. 5, 6 and 7. See also "section 3" in FIGS. 2 and 3. This section curves to the left, as shown in FIG. 2, in a curve with a radius from about 1 to about 4 inches and preferably from about 1 to about 3 inches. The extent of the arc of the curve is from about 30° to about 90° and preferably from about 45° to about 75°. As this third section curves to the left as shown in FIG. 2, it continues the curve upward of Section 2 as shown in FIG. 3. The radius of this upwardly curved portion and the extent of the arc of the curve is the same as for Section 2. The overall length of this section is from about 1 to about 4 inches.

At the end of this third section is the fourth section which is marked as "section 4" on FIG. 2. This section is also labeled against "section 4" on FIGS. 5, 6, 7 and 8. This fourth section comprises a curved section with a radius from about 0.5 to about 3.0 inches and preferably from about 0.5 to about 1.5 inches. The extent of the arc of the curve of this curved section is from about 30° to about 115° and preferably from about 45° to about 90°.

At the distal end of this fourth section is the fifth section which is a straight section. The length of the straight section is less than about 2.0 in. and preferably from about 0.2 to about 1.00 inches and more preferably from about 0.4 to about 0.6 inches in length, ending in the distal tip of the guiding introducer.

While the above described shape is preferred, the shape of the sections of the guiding introducer may be modified by use of one or more straight or curved sections as long as the overall, general shape of the guiding introducer is approximately as described above. In addition, the particular order of curves may be changed as long as the overall curvature of the guiding introducer delivers the bioptome or biopsy sheaths to approximately the same location as the guiding introducer above described as the preferred embodiment. Further, one or more curves of the instant application may be combined or split into additional curved or curved and straight sections as long as the general overall shape of the precurved, guiding introducer is maintained. The critical design feature of the guiding introducer is that it provides a stable platform supported by the walls of the cardiac anatomy to permit a biopsy forceps to be repeatedly advanced and withdrawn without the need for repositioning the guiding introducer.

The overall length of the guiding introducer is preferably about 30 to about 50 centimeters. The overall length of the guiding introducer can be extended as desired by medical practitioners but should not be longer than about 50 centimeters.

The distal tip of the guiding introducer may be and preferably is tapered to form a good transition with a dilator. This tapering is preferably less than 10° and more preferably from about 4° to about 7°. The guiding introducer preferably also preferably contains one or a plurality of radiopaque tip marker bands near the distal tip of the guiding introducer. This guiding introducer also preferably contains one or a plurality of vents near the distal tip of the guiding introducer, preferably three or four such vents. The vents are preferably located no more than about 1 inch from the distal tip of the guiding introducer and more preferably about 0.1 to about 1.0 inch from the distal tip. The size of these vents should be in the range of about 40 to about $60/1000$ of an inch in diameter. These vents are designed to prevent air from entering the guiding introducer caused by the withdrawal of the biopsy catheter contained within the guiding introducer in the event the distal end of the guiding introducer is occluded.

The guiding introducer may be made of any material suitable for use in humans which has a memory or permits distortion from and substantial return to the desired three dimensional shape. For the purpose of illustration and not limitation, the internal diameter of the guiding introducer may vary from about 5 to about 10 "French" respectively (1 French=$1/3$ of a millimeter). Such guiding introducer may also accept dilators and appropriate guidewires. Obviously, depending on the size of the bioptome, the internal diameter of the guiding introducer can be modified.

Variations in size and shape of the guiding introducer are also intended to encompass pediatric uses, although the preferred use is for adult human hearts. It is well recognized that pediatric uses may require reductions in size of the various sections of the guiding introducer without significant modifications to the overall shape or curve of the sections of the guiding introducer.

In addition, variations in size and shape of the guiding introducer are also intended to encompass specialized situations that sometimes occur in patients where their heart has been enlarged or rotated as a result of the transplant.

In operation, a modified Seldinger technique is normally used for the insertion of the catheter into the internal jugular or subclavian vein. The appropriate vessel is accessed by needle puncture. A soft, flexible tip of an appropriately sized guidewire is then inserted through and a short distance beyond the needle into the vessel. Firmly holding the guidewire in place, the needle is removed. The guidewire is then advanced through the vein through the superior vena cava into the right atrium and across the tricuspid valve into the right ventricle. With the guidewire in place, a dilator is then placed over the guidewire with the guiding introducer placed over the dilator. The dilator and guiding introducer generally form an assembly to be advanced together along the guidewire into the right atrium and across the tricuspid valve into the right ventricle. After insertion of the guiding introducer, the guidewire and dilator are withdrawn. The shape of guiding introducer places its distal tip only a short distance away from and directed at the septum. The biopsy forceps or bioptome is then advanced through the guiding introducer into the right ventricle where its jaws are open and the biopsy procedure is performed. The shape of the guiding introducer provides a stable platform supported by the walls of the cardiac anatomy to permit the biopsy forceps to be repeatedly advanced and withdrawn without repositioning the guiding introducer. After completion of the various biopsy procedures, the bioptome is withdrawn and then the guiding introducer is removed.

The precise placement of the bioptome in the right ventricle is important so that the biopsy sample can be taken at the proper location along the septum. In addition, by use of this particular shaped guiding introducer, introduction of the bioptome into the heart is quickly accomplished with reduced trauma to the patient and to the anatomical features of the patient's heart. In particular, the shape of the guiding introducer reduces the likelihood of damage to the leaflets of the tricuspid valve. The overall trauma to the patient is further reduced by reducing the average time necessary for the biopsy procedure from about 30 minutes to less than 10 minutes. Thus, the use of this guiding introducer results in an improved procedure with reduced discomfort to the patient.

It will be apparent from the foregoing that while particular forms of the invention have been illustrated and described, various modifications can be made without departing from the spirit or scope of the invention. Accordingly, it is not intended that this invention be limited except as by the appended claims.

We claim:

1. An endomyocardial biopsy system for use in a human heart comprising a precurved, shaped, lumened guiding introducer and a biopsy forceps, wherein the shape of the guiding introducer is three dimensional comprising curved and straight sections and wherein the biopsy forceps are inserted into the heart through the lumen of the guiding introducer and wherein a portion of the guiding introducer is shaped to conform to the anatomy of the right ventricle of the heart.

2. The system of claim 1 wherein the curved sections comprise a first curved section comprising a curve with a radius of about 2 to about 8 inches and an arc of the curve of about 20° to about 70°.

3. The system of claim 1 wherein the curved sections comprise a second curved section comprising a compound curve, curving with a radius of about 1 to about 4 inches and an arc of the curve from about 30° to about 90° and, also curving with a radius of about 1 to about 8 inches and an arc of the curve from about 20° to about 70°.

4. The system of claim 1 wherein the curved section comprises a third curved section comprising a curve with a radius of about 0.5 to about 3.0 inches and an arc of the curve from about 30° to about 115°.

5. The system of claim 1 wherein the straight sections comprise a straight section from about 0.2 to about 1.0 inch in length.

6. The system of claim 1 wherein the curved sections comprise a first, second and third curved section.

7. The system of claim 6 wherein the first curved section comprises a curve with a radius of about 4 to about 8 inches and an arc of the curve from about 20° to about 70°.

8. The system of claim 6 wherein the first curved section comprises a curve with a radius of about 4 to about 6 inches and an arc of the curve from about 40° to about 50°.

9. The system of claim 6 wherein the second curved section comprises a compound curve, curving with a radius of about 1 to about 4 inches and an arc of the curve from about 30° to about 90° and also curving with a radius of about 1 to about 8 inches and an arc of the curve from about 20° to about 70°.

10. The system of claim 6 wherein the second curved section comprises a compound curve, curving with a radius of about 1 to about 4 inches and an arc of the curve from about 45° to about 75° and also curving with a radius of about 1 to about 8 inches and an arc of the curve from about 20° to about 70°.

11. The system of claim 6 wherein the second curved section comprises a compound curve, curving with a radius of about 1 to about 3 inches and an arc of the curve from about 45° to about 75° and also curving with a radius of about 4 to about 6 inches and an arc of the curve from about 40° to about 50°.

12. The system of claim 6 wherein the third curved section comprises a curve with a radius of about 0.5 to about 3.0 inches and an arc of the curve from about 30° to about 115°.

13. The system of claim 6 wherein the third section comprises a curve with a radius of about 0.5 to about 1.5 inches and an arc of the curve from about 45° to about 90°.

14. The system of claim 1 wherein the curved sections comprise a first, second and third section and the straight sections comprise a straight section less than about 2 inches in length.

15. The system of claim 13 wherein the straight section is from about 0.2 to about 1.0 inches in length.

16. A precurved, shaped guiding introducer, wherein the shape of the introducer is three dimensional comprising a first, second and third curved sections and a straight section wherein the first curved section comprises a curve with a radius of about 2 to about 8 inches and an arc of the curve from about 20° to about 70°, wherein the second curved section comprises a compound curve, curving first with a radius from about 1 to about 4 inches and an arc of the curve from about 30° to about 90° and also curving with a radius of about 1 to about 8 inches and an arc of the curve from about 20° to about 70°, wherein the third curved section curves with a radius from about 0.5 to about 3.0 inches and an arc of the curve from about 30° to about 115° and wherein the straight section is less than about 2.0 inches in length.

17. A process for an endomyocardial biopsy procedure in the human heart comprising
   (a) introducing a precurved, shaped, lumened guiding introducer into a chamber of the human heart, wherein the shape of the guiding introducer is three dimensional, wherein the guiding introducer is shaped to conform to the anatomy of the right ventricle of the heart and wherein the guiding introducer comprises a series of curves and straight sections and wherein it comprises at least two curved sections,
   (b) introducing into the lumen of the guiding introducer a biopsy forceps,
   (c) advancing the biopsy forceps through the lumen of the guiding introducer until its distal portion extends out of the distal end of the guiding introducer,
   (d) removing a sample of tissue from a wall of the chamber of the heart, and
   (e) withdrawing the sample from the heart for biopsy.

18. The process of claim 16 wherein the curves of the guiding introducer comprise a first curved section with a radius of about 2 to about 8 inches and an arc of the curve from about 2° to about 70°.

19. The process of claim 1 wherein the curves of the guiding introducer comprise a compound curve, curving with a radius of about 1 to 4 inches with an arc of the curve from about 30° to about 90° and also curving with a radius of about 1 to about 8 inches and an arc of the curve from about 20° to about 70°.

20. The process of claim 16 wherein the curves of the guiding introducer comprise a third curved section with a radius of about 0.5 to about 3 inches and an arc of the curve from about 30° to about 115°.

21. The process of claim 16 wherein the straight section is from about 0.2 to about 1 inch in length.

22. The process of claim 16 wherein the guiding introducer comprises first, second and third curved sections and a straight section.

23. The process of claim 16 wherein the guiding introducer comprises a first, second and third curved section and a straight section, wherein the first curved section comprises a curve with a radius of about 2 to about 8 inches with an arc of the curve from about 20° to about 70°, wherein the second curved section comprises a compound curve, curving first with a radius from about 1 to about 4 inches with an arc of the curve from about 30° to about 90° and also curving with a radius of about 1 to about 8 inches and an arc of the curve from about 20° to about 70°, wherein the third curved section curves with a radius of about 0.5 to about 3.0 inches with an arc of the curve from about 30° to about 115° and wherein the straight section is less than about 2 inches in length.

* * * * *